United States Patent [19]

Bachmann et al.

[11] 4,159,319

[45] Jun. 26, 1979

[54] METHOD OF PREPARING AN ATTENUATED TRANSMISSIBLE GASTROENTERITIS (TGE) VIRUS STRAIN FOR USE IN LIVE VACCINES

[76] Inventors: Peter A. Bachmann; Anton Mayr, both of Veterinär-Str. 13, 8000 Munich 22, Fed. Rep. of Germany

[21] Appl. No.: 897,732

[22] Filed: Apr. 19, 1978

[30] Foreign Application Priority Data

Apr. 21, 1977 [NL] Netherlands ............................ 7704348

[51] Int. Cl.² .......................... A61K 39/12; C12K 7/00
[52] U.S. Cl. ............................................ 424/89; 195/1.3
[58] Field of Search ............................ 195/1.3; 424/89

[56] References Cited

U.S. PATENT DOCUMENTS

| 3,585,108 | 6/1971 | Welter | 195/1.3 |
| 3,704,203 | 11/1972 | Welter | 195/1.3 |
| 4,046,875 | 9/1977 | Djurickovic | 195/1.3 |

*Primary Examiner*—Sam Rosen
*Attorney, Agent, or Firm*—Norman N. Spain

[57] ABSTRACT

The invention relates to a method of preparing an attenuated virus strain, which can be used to protect pigs, and in particular piglets, against transmissible gastroenteritis (TGE).

7 Claims, No Drawings

METHOD OF PREPARING AN ATTENUATED TRANSMISSIBLE GASTROENTERITIS (TGE) VIRUS STRAIN FOR USE IN LIVE VACCINES

TGE is a very infectious pig disease occurring nearly everywhere in the world and causing considerble losses in pig breeding.

The disease TGE is nearly always fatal for piglets which are infected in the first few weeks after birth. Since active immunization is not yet possible at such an instant within that period, it has been endeavoured for some time already to find a method to provide a passive immunity to piglets through the sow.

Although a few methods are known for giving piglets a passive immunity through the colostrum of the mother animal (Belgian Patent Specification No. 669,881 and Netherlands Patent Application No. 68.09013), it is known from recent literature that passive immunity in piglets can be produced by oral infection of the sow with field strains of the TGE (that is to say with virulent virus), but attempts to produce this with virus strains attenuated by cell culture passages have failed or have given only a restricted degree of protection (Infection and Immunity, 1976 pp. 1642–1646). This is because by the use of serial passages not only the virulence but also the immunogenicity decrease considerably.

Since the administration of virulent virus to sows involves great risks, this is an undesired and unacceptable method of protecting piglets against TGE.

According to the invention it has been surprisingly found possible to obtain an attenuated, nonvirulent immunogenically active TGE virus by subjecting virulent TGE virus to a very large number of successive serial passages in thyroid gland cell cultures.

It has been found more in particular that an attenuated non-pathogenic, immunogenically active TGE virus strain is obtained by subjecting virulent virus to 250–350, preferably approximately 300 serial passages in cell cultures of swine thyroid gland tissue.

It is known that the immunity of piglets against TGE obtained through the colostrum of a sow infected with virulent virus depends on the IgA (immunoglobulin A)-antibody formation in the mammary glands (Amer. J. Vet Res. 36 (1975), 267–271).

It has furthermore been demonstrated that a sufficient amount of IgA antibodies is formed in the sow only if the virus has multiplied over the whole or nearly the whole length of the small intestine (E. H. Bohl et al., Infect. Immun. 11, (1975), 23–32 and E. H. Bohl et al., Infect Immun. 6 (1972), 289–301), Since the quantity of IgA antibodies decreases only slowly (F. J. Bourne et al. Immunol. 24, (1973), 157–162) it can be established with reference to the quantity of IgA antibodies which is secreted through colostrum and milk, whether a good passive immunization is possible in a given case.

When the virus attenuated according to the method of the invention is administered orally to sows, it continues to multiply along the whole intestinal tract of said animal so that the piglets of said sows are fully protected through the IgA antibodies of the colostrum against the results of an infection with virulent TGE virus. It is particularly surprising that a virus strain is still immunogenically active after such a large number of passages.

The IgA antibody titers of samples of the colostrum determined by the serum neutralizaton tests are recorded in the following table A. These samples were centrifuged, diluted with a physiological NaCl solution (1:10) and heated at 40° C. for 30 minutes. The pH was then brought at 4.6–4.65 by means of a mixture of equal volumes of 1 N HCl and 2 M acetic acid, stirring being carried out for 20 minutes. After centrifuging (12,000 g and 4° C.) the samples were dialysed overnight against 0.1 M tris-(hydroxymethyl)-aminomethane, 0.2 M NaCl which was brought at pH 8.0 by means of 1 N HCl. The samples were then concentrated to half in 5% Carbowax (mol. weight 20,000) and brought on a column (2.5×100 cm) with Sephadex-G-200. The eluation was carried out with tris-NaCl-buffer, pH 8.0.

TABLE A

| IgA-antibody titer | |
|---|---|
| number of passages | colostrum titer |
| 2 | 1:50 |
| 120 | 1:30 |
| 300 | 1:25 |
| 350 | 1:2.5 |

It has therefore been found that after the administration to sows of the 300th passage of the TGE virus attenuated according to the invention, a comparatively high content of IgA antibodies is found in the colostrum.

The invention will now be described in more detail.

The virulent virus from which an attenuated virus strain of the invention was formed, was isolated from an infected pig at the "Institut fur Mikrobiologie und Infektionskrankheiten der Tiere" in Munich. This very virulent virus strain which will be referred to hereinafter as B1-strain was directly isolated in swine thyroid gland tissue.

Cell cultures of swine thyroid gland tissue were prepared by using thyroid glands from the slaughter-house of Munich. The thyroid glands, after removing the envelope and sterilization of the surface twice with 95% alcohol), were cut into 1–2 mm pieces and washed three times in PBS (phosphate buffered saline). A 0.37% trypsine-PBS solution (without $Ca^{2+}$ and $Mg^{2+}$) was added to the tissue pieces thus obtained and a fractionated trypsine treatment was then carried out at 37° C. The first two trypsine fractions were discarded (after a treatment duration of 1 hour) and the fractions 3 and 4 (treatment duration 1.5 hours) were filtered and stored at 4° C. The trypsine activity was inhibited by the addition of serum. After termination of this treatment, the cell trypsine suspension was centrifuged for 10 minutes (500 g). The supernatant liquid was discarded and the sediment was suspended in PBS and again centrifuged. The cell sediment was then taken up in 10 ml of culture medium. The culture medium used was Earle's salt solution. However, other suitable culture media may also be used. The growth medium contained 10% calf serum and the maintenance medium 5%. The medium furthermore contained 50 ml of lactalbumine hydrolysate per liter of medium and possibly one or more antibiotics. The growth of the cells took place in normal culture vessels, for example flat glass or plastics bottles. The culture medium was replaced after 2–3 days. After a culture at 37° C. for 4–6 days, the primary cell cultures were usually closed with a cell layer.

Secondary cell cultures of swine thyroid glands were used for the passages of the B1 strain of the TGE virus in the above-mentioned cells and for the determination of the infectious capacity of the virus in the various parts of the small intestine. Said secondary cell cultures were obtained by again sowing the primary cell cultures in the ratio 1:2.

The attenuation of the virus was carried out by 250–350 serial passages in secondary swine thyroid gland tissue cells at a temperature of 37° C. Said serial passages were carried out in the usual manner. On the basis of the cytopathogenic effect and by means of virus titrations it was established that the virus titer was usually maximum after an incubation of 24–28 hours.

The invention will be further elucidated by means of the following experiments.

EXPERIMENT A

In order to determine the influence of serial passage in swine thyroid gland tissue on the virulence of the virus, 2 ml of the 2nd ($2 \times 10^4$ PFU/ml), 120th ($2 \times 10^6$ PFU/ml), 250th ($8 \times 10^6$ PFU/ml), 300th ($4 \times 10^6$ PFU/ml) and the 350th ($4 \times 10^6$ PFU/ml) passage attenuated virus were administered to two individual piglets from the litter of newly born piglets. The titers of the various passage levels are expressed in plaque-forming units per ml (PFU/ml). At an age of 1–2 days the experimental animals used were taken away from sows which had no neutralizing antibodies against TGE virus and fed by bottle. On the second day of the life the piglets were infected orally by the administration of 2 ml of one of the above-mentioned serial passage levels of the virus. 2 ml of culture medium were given to 10 control piglets.

The course of the clinical disease process was checked twice daily. When the piglets were still alive on the tenth day, a blood sample was taken for the antibody determination. Antibodies were determined by means of the serum neutralization test by means of the microtiter method (K. H. Witte, Arch. ges. Virusforsch. 33 (1971), 171–176).

incubation time was established which increased to 80 hours for the 300th passage.

After infection with the 2nd, 120th and 250th passage attenuated virus the animals got diarrhea which continued for a few days. Piglets which had received the 300th passage attenuated virus produced faeces of a sticky consistency only for a few days, while piglets who had received the 350th passage attenuated virus showed no symptom whatsoever of the disease.

Piglets which were infected with the 2nd passage of the virus strain died 1–2 days after administration of the virus. None of the 6 piglets survived the infection after administration of the 120th passage attenuated virus. One out of the four piglets infected with the 250th passage attenuated virus survived. All animals which had received the 300th passage attenuated virus survived the infection, as well as the piglets to which the 350th passage attenuated virus has been administered.

It appears from these results that the virulence up to the 250th passage attenuated virus had only been attenuated slightly so that an infection caused thereby usually resulted in a serious disease phenomena followed by death.

EXPERIMENT B

This experiment was carried out to determine where the virus of the various passage levels of the virus attenuated according to the invention multiplies in the small intestine. For this purpose, the same passage levels as in experiment A were administered to newly born piglets in an identical manner. Immediately after the observation of the first symptoms of a typical TGE virus infection, the piglets which had been kept isolated and been infected individually were killed. Beginning with the duodenum, totally 10 samples of the small intestine were taken at uniform distances of 25–35 cm. These

TABLE B

| | | Clinical symptoms on day. . . | | | | | | | | | |
|---|---|---|---|---|---|---|---|---|---|---|---|
| Number of passages | piglet No. | 1 | 2 | 3 | 4 | 5 | 6 | 7 | 8 | 9 | 10 |
| 2 | 13 | – | | | | | | | | | |
| | 14 | – | | +++ | X | | | | | | |
| 120 | 15 | – | – | ++ | ++ | +++ | X | | | | |
| | 16 | – | – | + | ++ | ++ | +++ | ++ | +++ | X | |
| | 17 | – | – | – | ++ | +++ | +++ | X | | | |
| | 18 | – | – | + | + | ++ | ++ | X | | | |
| | 19 | – | – | ++ | +++ | +++ | X | | | | |
| | 20 | – | – | + | ++ | ++ | ++ | ++ | X | | |
| 250 | 85 | – | – | – | ++ | ++ | +++ | X | | | |
| | 86 | – | – | – | +++ | +++ | X | | | | |
| | 87 | – | – | – | + | ++ | ++ | ++ | X | | |
| | 88 | – | – | – | +++ | +++ | + | + | – | – | 1:128 |
| 300 | 51 | – | – | – | – | – | (+) | – | – | – | 1:8 |
| | 52 | – | – | – | – | – | (+) | – | – | – | 1:16 |
| | 53 | – | – | – | – | – | (+) | – | – | – | 1:4 |
| | 54 | – | – | – | – | – | (+) | – | – | – | 1:64 |
| 350 | 76 | – | – | – | – | – | – | – | | | |
| | 77 | – | – | – | – | – | – | – | | | |
| | 78 | – | – | – | – | – | – | – | | | |
| | 79 | – | – | – | – | – | – | – | | | |
| | 80 | – | – | – | – | – | – | – | | | |
| | 81 | – | – | – | – | – | – | – | | | |
| | 82 | – | – | – | – | – | – | – | | | |
| | 83 | – | – | – | – | – | – | – | | | |

\+ to +++ slight to strong diarrhoea
X dead
– no phenomena

The first appearance of diarrhea was considered as the end of the incubation time. Vomiting occurred only in piglets which had received the 2nd passage. For this passage attenuated virus the incubation time was 16–18 hours. At the higher passage levels an extension of the samples were used to determine the virus titer spread over the various parts of the small intestine. The titer was determined after homogenization of the sample in a mortar and centrifuging the 10% suspension in PBS. Of the supernatant liquid, 10-fold dilutions were then prepared of which each time 4 culture tubes with swine thyroid gland cells were incubated with 0.2 ml of the individual samples. After an incubation of 7 days at 37° C., the cytopathogenic effect (CPE) was read and the titer was determined according to the method of Kärber (Naunyn-Schmiedebergs Arch. Exp. Pathol. Pharmakol. 162 (1931), 480–482).

TABLE C

| Number of passages | Incubation time | Virus titer in intestine section No. | Number of passages | Incubation time | Virus titer in intestine section No. |
|---|---|---|---|---|---|
|  |  | 1:neg |  |  | 1:1.5 |
|  |  | 2:0.5 |  |  | 2:1.0 |
|  |  | 3:0.5 |  |  | 3:3.0 |
|  |  | 4:0.5 |  | 76 hours | 4:3.0 |
| 2 | 16 hours | 5:1.0 | 300 | (1st exp.) | 5:4.0 |
|  | (1st exp.) | 6:05 |  | 80 hours | 6:35 |
|  | 18 hours | 7:05 |  | (2nd exp.) | 7:2.5 |
|  | (2nd exp.) | 8:05 |  |  | 8:3.5 |
|  |  | 9:0.5 |  |  | 9:3.5 |
|  |  | 10:0.5 |  |  | 10:4.5 |
|  |  | 1:2.0 |  |  | 1:neg |
|  |  | 2:2.5 |  |  | 2:neg |
|  |  | 3:2.5 |  |  | 3:neg |
|  |  | 4:3.5 |  |  | 4:neg |
| 120 | 30 hours | 5:3.0 | 350 | no | 5:2.5 |
|  | (1st exp.) | 6:4.5 |  | symptons | 6:3.0 |
|  | 34 hours | 7:3.0 |  |  | 7:0.5 |
|  | (2nd exp.) | 8:2.5 |  |  | 8:neg |
|  |  | 9:3.0 |  |  | 9:neg |
|  |  | 10:2.5 |  |  | 10:neg |
|  |  | 1:neg | control |  | 1–10:neg |
|  |  | 2:1.5 | not |  |  |
|  |  | 3:1.5 | infected |  |  |
| 250 | 40 hours | 4:20 |  | no |  |
|  | (1st exp.) | 5:3.0 |  | symptons |  |
|  | 52 hours | 6:2.0 |  |  |  |
|  | (2nd exp.) | 7:2.5 |  |  |  |
|  |  | 8:3.5 |  |  |  |
|  |  | 9:2.5 |  |  |  |
|  |  | 10:2.5 |  |  |  |

As appears from the results recorded in the above table C, the virulent virus multiplied from the 2nd passage in the whole small intestine, the duodenum excepted. The same applies to virus of the 120th and 250th passage. For the 2nd passage the virus titers were between 0.5 and 1.0 log 10 TCID$_{50}$/0.2 ml, while the titers of the 120th passage were between 2.0 and 4.5 and 4.5 log 10 TCID$_{50}$/0.2 ml. Similar titers were found for the viruses of the 250th and 300th passages. On the contrary, multiplication of the virus could be demonstrated only in the central part of the jejunum after administration of the 350th passage.

EXPERIMENT C

With this experiment it is demonstrated that virus of the 300th passage obtained according to the invention by administration to a pregnant sow protects the piglets of this sow effectively against infection with virulent TGE virus (Miller-strain).

The virulent test virus was obtained by preparing a 10% suspension of finely rubbed small intestine in PBS of virus of the Miller strain after three passages through piglets. After centrifuging, dividing in quantities of 2 ml and freezing at −70° C., said virus material was used to infect the piglets on the third day of life. For this purpose, 1 ml of such a dilution of the virus suspension was administered to the piglets that this corresponded to 100–1000 PID (pig infective dose).

TABLE D

Neutralization titer of the serum of the sow and the piglets after passive immunization with the 300th passage of the TGE B1-strain.

| Piglet No. | Day of birth | Number of days after birth | | |
|---|---|---|---|---|
|  |  | 3 | 7 | 14 |
| 121 | <1:2 | 1:16 | 1:16 | 1:16 |
| 122 | <1:2 | 1:16 | 1:32 | 1:16 |
| 123 | <1:2 | 1:8 | 1:16 | 1:8 |
| 124 | <1:2 | 1:32 | 1:16 | 1:16 |
| sow | 1:8 | 1:16 | 1:32 | 1:64 |

In this experiment the virus of the 300th passage was administered twice in a quantity of 5 ml orally in a capsule resistant against stomach acid.

All piglets survived this challenge test.

What is claimed is:

1. A method of preparing a vaccine containing a live, attenuated non-virulent, immunogenically active TGE virus strain, comprising isolating a virulent TGE virus strain directly on swine thyroid gland tissue, subjecting said strain to a large number of passages in said tissue to attenuate said virus while maintaining said virus immunogenically active and formulating said attenuated virus strain into a vaccine.

2. The method of claim 1 wherein the virulent strain is subjected to 250–350 passages at 37° C.

3. The method of claim 2 wherein the B1 strain is used as the virulent virus strain.

4. The method of claim 2 wherein the virus in each passage is incubated at 37° C. for 1–2 days, the liquid containing the virus is then separated and is then again subjected to passage in the cells of the swine thyroid gland tissue.

5. A method of immunogenizing a piglet from infection by virulent TGE virus comprising administering to the sow of said piglet, while pregnant with said piglet, a vaccine containing live attenuated non-virulent, immunogenically active TGE virus obtained by the method of claim 1.

6. The method of claim 5 wherein the vaccine is orally administered.

7. An oral vaccine suitable for oral administration to a pregnant sow for immunity against virulent TGE virus infection of a piglet of said sow comprising a suspension of live attenuated non-virulent, immunogenically active TGE virus obtained by the method of claim 1.

* * * * *